United States Patent
Shin et al.

(10) Patent No.: US 11,202,741 B2
(45) Date of Patent: Dec. 21, 2021

(54) SELF-RESTORABLE CORE-SHELL CAPSULE

(71) Applicant: AMOREPACIFIC CORPORATION, Seoul (KR)

(72) Inventors: Ji Sik Shin, Yongin-si (KR); Young Suk Cho, Yongin-si (KR); Seung Han Park, Yongin-si (KR); Byung Geun Chae, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/758,499

(22) PCT Filed: Sep. 26, 2016

(86) PCT No.: PCT/KR2016/010769
§ 371 (c)(1),
(2) Date: Mar. 8, 2018

(87) PCT Pub. No.: WO2017/057884
PCT Pub. Date: Apr. 6, 2017

(65) Prior Publication Data
US 2018/0243183 A1 Aug. 30, 2018

(30) Foreign Application Priority Data

Sep. 30, 2015 (KR) .................. 10-2015-0137589
Sep. 23, 2016 (KR) .................. 10-2016-0122122

(51) Int. Cl.
*A61K 8/11* (2006.01)
*A61Q 19/00* (2006.01)
(Continued)

(52) U.S. Cl.
CPC .............. *A61K 8/11* (2013.01); *A61K 8/34* (2013.01); *A61K 8/342* (2013.01); *A61K 8/731* (2013.01);
(Continued)

(58) Field of Classification Search
CPC . A61K 8/11; A61K 8/34; A61K 8/342; A61K 8/731; A61K 8/8152; A61K 8/92;
(Continued)

(56) References Cited

U.S. PATENT DOCUMENTS 4,892,740 A * 1/1990 Takasima .............. A61K 9/5089
424/474
5,817,155 A * 10/1998 Yasuda .................... A61K 8/06
8/406
(Continued)

FOREIGN PATENT DOCUMENTS

CN          1929820 A      3/2007
CN       101309746 A      11/2008
(Continued)

OTHER PUBLICATIONS

Shirakawa, Kuniko et al., Journal of Cosmetics, Dermatological Sciences and Applications, 2013, 3, pp. 49-54 (Year: 2013).*
(Continued)

*Primary Examiner* — Ernst V Arnold
(74) *Attorney, Agent, or Firm* — McCoy Russell LLP

(57) ABSTRACT

The present invention relates to a core-shell capsule comprising: a core comprising an oil, a solvent satisfying relational expression 1 below, and a water-insoluble polymer compound dissolved in the solvent; and a water-insoluble polymer shell enclosing the core.

$0.01 \leq C_A/C_B \leq 100$   [Relational expression 1]

(in relational expression 1, $C_A/C_B$ is the distribution coefficient of solvent, and when the solvent is dissolved in oil and
(Continued)

water to reach equilibrium, $C_A$ is the concentration of the solvent dissolved in the oil and $C_B$ is the concentration of the solvent dissolved in water).

12 Claims, 3 Drawing Sheets

(51) Int. Cl.
    *A61K 8/34*     (2006.01)
    *A61K 8/81*     (2006.01)
    *B01J 13/02*     (2006.01)
    *A61K 8/92*     (2006.01)
    *A61K 8/73*     (2006.01)
    *A61Q 1/12*     (2006.01)
    *B01J 13/06*     (2006.01)

(52) U.S. Cl.
    CPC .............. *A61K 8/8152* (2013.01); *A61K 8/92* (2013.01); *A61Q 1/12* (2013.01); *A61Q 19/00* (2013.01); *A61Q 19/007* (2013.01); *B01J 13/02* (2013.01); *B01J 13/06* (2013.01); *A61K 2800/10* (2013.01); *A61K 2800/56* (2013.01); *A61K 2800/652* (2013.01)

(58) Field of Classification Search
    CPC ............ A61K 2800/10; A61K 2800/56; A61K 2800/652; A61Q 1/12; A61Q 19/00; A61Q 19/007; B01L 13/06; B01J 13/02; B01J 13/06
    See application file for complete search history.

(56) References Cited

U.S. PATENT DOCUMENTS

| | | | |
|---|---|---|---|
| 6,197,348 B1 * | 3/2001 | Morelia | A61P 25/18 424/497 |
| 2005/0026801 A1 * | 2/2005 | Broeckx | B01J 13/02 510/276 |
| 2006/0276356 A1 * | 12/2006 | Panandiker | C11D 7/3281 510/100 |
| 2006/0292193 A1 | 12/2006 | Lee et al. | |
| 2009/0005486 A1 * | 1/2009 | Raravikar | C08K 4/36 |
| 2010/0086651 A1 * | 4/2010 | Dardelle | A61K 8/11 426/89 |
| 2012/0148514 A1 * | 6/2012 | Musa | A01N 53/00 424/60 |
| 2012/0301546 A1 * | 11/2012 | Hassan | A61K 9/4825 424/465 |
| 2014/0182481 A1 * | 7/2014 | Boday | C11C 3/00 |
| 2014/0227329 A1 | 8/2014 | Habar | |
| 2015/0344365 A1 * | 12/2015 | Keung | C04B 14/06 |

FOREIGN PATENT DOCUMENTS

| | | |
|---|---|---|
| CN | 104873419 A | 9/2015 |
| KR | 950008517 B1 | 7/1995 |
| KR | 20040084364 A | 10/2004 |
| KR | 1020070017128 A | 2/2007 |
| KR | 101168038 B1 | 7/2012 |

OTHER PUBLICATIONS

EWG's Skin Deep, Octyldodecanol, Jul. 5, 2014, pp. 1-2 (Year: 2014).*
Li et al. (Scientific Reports 2017;7:6302: 10 pages) (Year: 2017).*
Xu et al. (Scientific Reports 2020; 10:4549:10 pages) (Year: 2020).*
Heng et al. Handbook of Cosmoceutical Excipients and their Safeties; 2014; p. 82). (Year: 2014).*
White, S. et al., "Autonomic healing of polymer composites," Nature, vol. 409, Published Online Feb. 15, 2001, 5 pages.
Yuan, Y. et al., "Self Healing in polymers and polymer composites. Concepts, realization and outlook: A review," eXPRESS Polymer Letters, vol. 2, No. 4, Apr. 2008, 14 pages.
Blaiszik, B. et al., "Self-Healing Polymers and Composites," Annual Review of Materials Research, vol. 40, Apr. 5, 2010, 36 pages.
Koh, E. et al., "Polyurethane microcapsules for self-healing paint coatings," RSC Advances, vol. 4, No. 31, Apr. 1, 2014, 11 pages.
ISA Korean Intellectual Property Office, International Search Report Issued in Application No. PCT/KR2016/010769, dated Jan. 13, 2017, WIPO, 4 pages.
European Patent Office, Extended European Search Report Issued in Application No. 16852030.2, dated Apr. 3, 2019, Germany, 10 pages.

* cited by examiner

A) Initial state before applying impact

B) Final state after applying repeated impact

SELF-RESTORABLE CORE-SHELL CAPSULE

CROSS-REFERENCE TO RELATED APPLICATIONS

The present application is a U.S. National Phase of International Patent Application Serial No. PCT/KR2016/010769 entitled "SELF-RESTORABLE CORE-SHELL CAPSULE," filed on Sep. 26, 2016. International Patent Application Serial No. PCT/KR2016/010769 claims priority to Korean Patent Application No. 10-2015-0137589, filed on Sep. 30, 2015, and Korean Patent Application No. 10-2016-0122122, filed on Sep. 23, 2016. The entire contents of each of the above-cited applications are hereby incorporated by reference in their entirety for all purposes.

TECHNICAL FIELD

The present invention relates to a self-healable core-shell capsule.

BACKGROUND ART

Self-healing means that materials such as polymers damaged by an external environment may detect defects by themselves to restore their structure, and also to recover the original function, and since the damage of the materials causes loss of physical properties and function of the materials themselves, and has a great impact on durability and performance persistence of an entire product, there is a rapidly growing interest in development of self-healing materials allowing fundamental restoration of structure and function of materials as well as suppressing damage.

As one of the self-healable materials, S. R. White, etc., introduced a self-healing system healing damage of thermosetting materials, using microcapsules containing monomers (Non-patent document 1). This self-healing system has a form in which liquid phase monomers are encapsulated, and these capsules are present to be dispersed in matrix materials together with catalyst particles, and in the case that microcapsules in the matrix are damaged by an external impact and the like, the monomers contained in the capsules flow out to be polymerized in the presence of the catalyst in the matrix, so that the capsules and matrix may be restored by themselves.

However, in this case, there are fundamental limitations in that the catalyst to be used is expensive, physical property resilience reaches only about 75% due to interfacial heterogeneity at the healing site, and most of all, a portion of once healed is not available for re-healing.

(Non-patent document 1) S. R. White, N. R. Sottos, P. H. Geubelle, J. S. Moore, M. R. Kessler, S. R. Sriram, E. N. Brown, and S. Viswanathan, Nature, 409, 794 (2001).

DISCLOSURE

Technical Problem

The present invention was made for solving the above problems, and an object of the present invention is to provide a core-shell capsule having excellent self-healing capability to restore the shape of the capsule, when a physical crack occurs in the capsule.

Technical Solution

The present invention relates to a core-shell capsule including: a core including an oil, a solvent satisfying the following Equation 1, and a water-insoluble polymer compound dissolved in the solvent; and a water-insoluble polymer shell surrounding the core.

$$0.01 \leq C_A/C_B \leq 100 \quad \text{[Equation 1]}$$

wherein $C_A/C_B$ is a distribution coefficient of the solvent, in which when the solvent is dissolved in oil and water to reach equilibrium, $C_A$ is a concentration of the solvent dissolved in the oil, and $C_B$ is a concentration of the solvent dissolved in the water.

In another general aspect, a cosmetic composition includes the core-shell capsules.

Advantageous Effects

The core-shell capsule according to the present invention has a merit of restoring the original form by itself to maintain a stable capsule shape, when a physical crack occurs in the capsule by an external impact, severe temperature change, or the like.

In addition, as the capsule allows self-healing, the core material inside of the capsule may not be influenced, such as degenerated by an external environment, and thus, the present invention has a merit of maintaining the efficacy of the core for a long time.

BEST MODE

Figure 1:
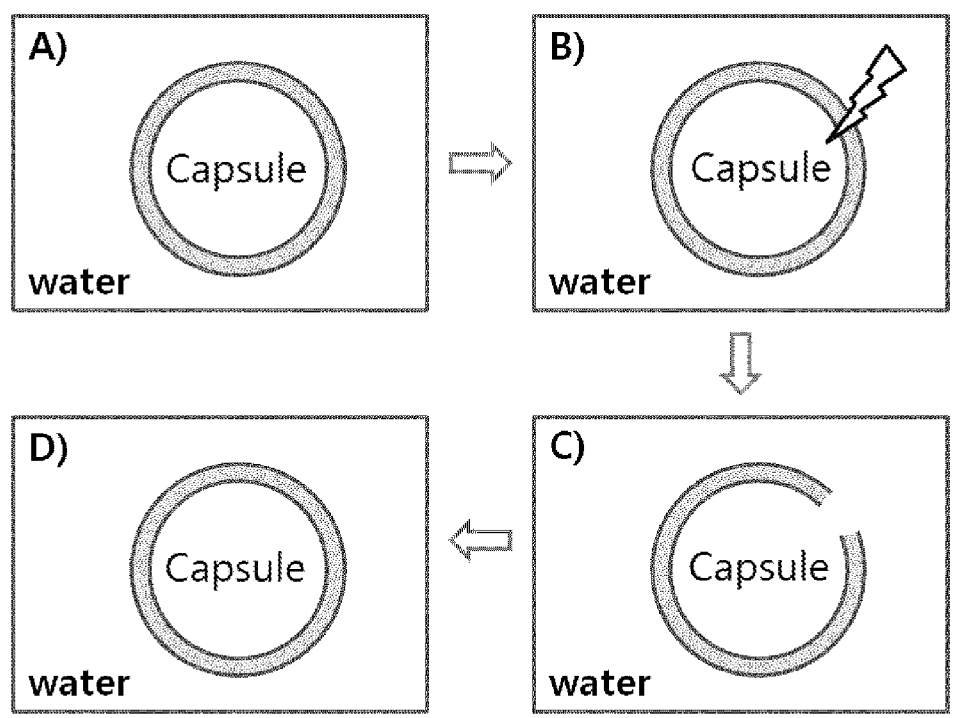
FIG. 1 illustrates self-healing capacity of a core-shell capsule according to an exemplary embodiment of the present invention, in which A) represents an initial core-shell capsule, B) represents that the capsule is subjected to an external impact, C) represents that the shell is damaged, and D) represents self-healing of the shell by effluence of an internal material.

Hereinafter, the core-shell capsule according to the present invention will be described in detail with reference to the accompanying drawings. The drawings to be provided below are provided by way of example so that the idea of the present invention can be sufficiently transferred to a person skilled in the art to which the present invention pertains. Therefore, the present invention is not limited to the drawings provided below but may be modified in many different forms. In addition, the drawings suggested below will be exaggerated in order to clear the spirit and scope of the present invention. In addition, like reference numerals denote like elements throughout the specification.

Technical terms and scientific terms used herein have the general meaning understood by those skilled in the art to which the present invention pertains unless otherwise defined, and a description for the known function and configuration unnecessary obscuring the gist of the present invention will be omitted in the following description and the accompanying drawings.

The present invention relates to a core-shell capsule which may restore the original form by itself to maintain a stable capsule shape, when a physical crack occurs in the capsule by an external impact, severe temperature change, or the like.

More specifically, in the core, a water-insoluble polymer compound which is a raw material of a polymer shell remains in a dissolved state, and when a crack occurs in the polymer shell, the water-insoluble polymer compound dissolved in the core is partially precipitated in the cracked portion of the shell by an external environment to restore the cracked portion of the shell, thereby self-healing the capsule shape. Accordingly, the capsule may be self-healed by itself even in the case of the damage by an external impact, severe temperature change, or the like, and thus, may have very high stability. In addition, since self-healing is possible, the core material inside of the capsule may not be influenced such as degenerated by an external environment, thereby maintaining the efficacy of the core for a long time, and since an oil which is one of the core materials may be stably positioned inside of each capsule, the oil is prevented from coalescing, so that it is not easily phase-separated. As another merit of the self-healing capability, a damaged capsule is self-healed to maintain its original form, thereby having an excellent appearance, and the maintenance of a capsule shape provides a unique sense of use.

Specifically, the core-shell capsule according to an exemplary embodiment of the present invention may include: a core including an oil, a solvent satisfying the following Equation 1, and a water-insoluble polymer compound dissolved in the solvent; and a water-insoluble polymer shell surrounding the core:

$$0.01 \leq C_A/C_B \leq 100 \quad \text{[Equation 1]}$$

wherein $C_A/C_B$ is a distribution coefficient of the solvent, in which when the solvent is dissolved in oil and water to reach equilibrium, $C_A$ is a concentration of the solvent dissolved in the oil, and $C_B$ is a concentration of the solvent dissolved in the water.

For enabling the self-healing, a solvent which dissolves the water-insoluble polymer compound well, and satisfies Equation 1 should be well selected. Equation 1 relates to a distribution coefficient of a solvent, and when a crack occurs in the polymer shell, the solvent according to the present invention has the distribution coefficient satisfying Equation 1, so that it may be diffused to the external phase such as water, etc., and the water-insoluble polymer compound dissolved in the solvent is diffused together with the diffused solvent to flow out to the outside. Here, the water-insoluble polymer compound flowing out to the outside of the core may be precipitated by an external environment such as water to restore the cracked part of the polymer shell. In addition, by using the solvent satisfying Equation 1, a hard polymer shell may be formed, when forming the capsule, and a capsule having high stability may be prepared.

However, when the distribution coefficient of the solvent is more than 100, the water-insoluble polymer compound dissolved in the core is difficult to flow out to the outside of the core, so that the capsule is not well formed, or self-healing is not well done, and when the distribution coefficient is less than 0.01, the solvent and the water-insoluble polymer compound dissolved in the solvent all exit to the external phase such as water, etc. before shell restoration, or shell restoration is possible, but the solvent and the water-insoluble polymer compound dissolved in the solvent all exit to the external phase such as water, so that the self-healing capability is limited to once.

Preferably, the solvent according to an exemplary embodiment may satisfy the following Equation 1-1:

$$0.1 \leq C_A/C_B \leq 10 \quad \text{[Equation 1-1]}$$

wherein $C_A/C_B$ is a distribution coefficient of the solvent, in which when the solvent is dissolved in oil and water to reach equilibrium, $C_A$ is a concentration of the solvent dissolved in the oil, and $C_B$ is a concentration of the solvent dissolved in the water.

By using the solvent having the distribution coefficient satisfying the above range, the present invention has a merit in that the solvent and the polymer compound dissolved in the solvent are diffused to the external phase when the capsule is damaged, thereby recovering the damaged part of the capsule more effectively, and also the diffusion to the outside is not so rapid, so that the self-healing capability is not limited to once, but may be maintained for several times to several hundred times. The distribution coefficient of the solvent may be more preferably $C_A/C_B$ 0.1 to 3, particularly preferably 0.2 to 1.

In an exemplary embodiment of the present invention, the solvent may be any one or two or more selected from the group consisting of alcohol-based solvents, ketone-based solvents and the like. Specifically, the alcohol-based solvent may be a linear or branched alcohol-based solvent having 1 to 22 carbon atoms, and the ketone-based solvent may be a linear or branched ketone-based solvent having 3 to 10 carbon atoms. As a non-limited specific example, the alcohol-based solvent may be any one or two or more selected from the group consisting of methanol, ethanol, isopropyl alcohol, n-propyl alcohol, octyl dodecanol and the like, and the ketone-based solvent may be any one or two or more selected from the group consisting of acetone, methylethyl ketone, methylisobutyl ketone and the like, but not limited thereto. In the present invention, when the core-shell capsule is applied as a cosmetic composition, a particularly preferred solvent may be ethanol.

In addition, the solvent according to an exemplary embodiment of the present invention may have a boiling point of 50° C. or more. When the boiling point is less than 50° C. which is unduly low, the solvent in the capsule is easily evaporated, so that the water-insoluble polymer compound may be precipitated inside of the capsule, and as the solvent is not diffused to the outside of the capsule even in the case that a crack occurs in the polymer shell, the water-insoluble polymer compound is difficult to be in contact with an external phase such as water, etc. in the cracked part, and thus, the polymer shell may be difficult to be formed. The upper limit of the boiling point is not particularly limited, but as a non-limited example, the boiling point may be 300° C. or less.

The water-insoluble polymer compound according to an exemplary embodiment of the present invention is, as described above, dissolved in the core which is an internal phase, and flows from the inside to the outside of the capsule through the cracked part of the shell, so as to be precipitated as a polymer material by an external phase such as water, etc., when the capsule is damaged, thereby restoring the damaged capsule film (polymer shell). Accordingly, it is preferred to select the water-insoluble polymer compound which is easily dissolved in the solvent, and not dissolved in an external phase such as water, etc.

As an example, the water-insoluble polymer compound may be any one or two or more selected from the group consisting of cellulose-based polymer compounds, polystyrene-based polymer compounds, acrylate-based polymer compounds and the like. As a non-limited specific example, the cellulose-based polymer compound may be any one or two or more selected from the group consisting of ethyl cellulose, cellulose acetate propionate, cellulose acetate butyrate and the like, the polystyrene-based polymer compound may be any one or two or more selected from the group consisting of polystyrene, poly p-methylstyrene, poly m-methylstyrene, poly p-ethylstyrene, poly m-ethylstyrene, poly p-chlorostyrene, poly m-chlorostyrene, poly p-chloromethylstyrene, poly m-chloromethylstyrene, poly p-butoxystyrene, poly m-butoxystyrene, poly t-butoxystyrene and the like, and the acrylate-based polymer compound may be any one or two or more selected from the group consisting of polymethyl(meth)acrylate, polyethyl(meth)acrylate, polypropyl(meth)acrylate, poly n-butyl(meth)acrylate, polyisobutyl(meth)acrylate, poly t-butyl(meth)acrylate, poly 2-ethylhexyl(meth)acrylate, poly n-octyl(meth)acrylate, polylauryl(meth)acrylate, polystearyl(meth)acrylate, poly 2-hydroxyethyl(meth)acrylate, polyethyleneglycol(meth)acrylate, methoxypolyethyleneglycol(meth)acrylate, polyglycidyl(meth)acrylate, polydimethylaminoethyl(meth)acrylate, polydiethylaminoethyl(meth)acrylate and the like, but not limited thereto. In the present invention, when the core-shell capsule is applied as a cosmetic composition, the particularly preferred water-insoluble polymer compound may be a cellulose-based polymer compound, and most preferably ethylcellulose.

In addition, in the present invention, in order for the core-shell capsule to have self-healing capability, it is necessary to properly adjust the contents of the water-insoluble polymer compound and the solvent in the core. As an example, the weight ratio of the water-insoluble polymer compound:solvent in the core may be 1:0.5 to 100. Within this range, the core-shell capsule may have excellent self-healing capability. Preferably the weight ratio of the water-insoluble polymer compound:solvent may be 1:1 to 50, more preferably the weight ratio of the water-insoluble polymer compound:solvent may be 1:3 to 10. When the amount of the water-insoluble polymer compound relative to the solvent is unduly small, even in the case that the solvent and the water-insoluble polymer compound dissolved in the solvent flow out to the external phase by damage of the capsule, the amount of the precipitated water-insoluble polymer compound is insignificant, so that the restoration of the damaged shell may be difficult, and when the amount of the water-insoluble polymer compound relative to the solvent is unduly large, the water-insoluble polymer compound may not be completely dissolved in the solvent, and the solvent may be partially diffused when the capsule is formed, thereby making the formation of the shell difficult.

The oil according to an exemplary embodiment of the present invention may be used without particular limitation as long as it is commonly used in the art for applying the core-shell capsule. As an example, in the case that the oil is applied as a cosmetic composition, it may be any one or two or more selected from the group consisting of a silicone-based oil, a hydrocarbon-based oil, an ester-based oil and the like. More specifically, the silicone-based oil may include cyclopentasiloxane, cyclohexasiloxane, cycloheptasiloxane, cyclomethicone, cyclophenylmethicone, cyclotetrasiloxane, cyclotrisiloxane, dimethicone, caprildimethicone, caprilyltrimethicone, caprilylmethicone, cetearylmethicone, hexadecylmethicone, hexylmethicone, laurylmethicone, miristylmethicone, phenylmethicone, stearylmethicone, stearyldimethicone, trifluoropropylmethicone, cetyldimethicone, dimethylpolysiloxane, methylphenylpolysiloxane, decamethylcyclopentasiloxane, methyltrimethicone, phenyltrimethicone and the like, but not limited thereto. The hydrocarbon-based oil may include an paraffin-based hydrocarbon oil, an olefin-based hydrocarbon oil, an aliphatic, cycloaliphatic or aromatic hydrocarbon oil and the like, and as a non-limited example, n-octane, n-nonane, n-decane, n-undecane, n-dodecane, n-tridecane, n-tetradecane, n-pentadecane, n-hexadecane, n-heptadecane, n-octadecane, vaseline, paraffin, isoparaffin, ceresin, squalane, squalene, polybutene, polydecene, polyisoprene or the like may be listed, but not limited thereto. The ester-based oil may include ascorbyl palmitate, ascorbyl linoleate, ascorbyl stearate, distearyl maleate, benzyl benzoate, benzyl laurate, butylene glycol dicaprylate/dicaprate, butylene glycol diisononanoate, butylene glycol laurate, butylene glycol stearate, butyl isostearate, cetearyl isononanoate, cetearyl nonanoate, cetyl caprylate, cetylethyl hexanoate, cetyl isononanoate, ethylhexyl caprylate/caprate, ethylhexyl isononanoate, ethylhexyl isostearate, ethylhexyl laurate, hexyl laurate, octyldodecyl isostearate, isopropyl isostearate, isostearyl isononanoate, isostearyl isostearate, isocetylethyl hexanoate, neopentyl glycol dicaprate, neopentyl glycol diethyl hexanoate, neopentyl glycol diisononanoate, neopentyl glycol diisostearate, pentaerythrityl stearate, pentaerythrityl tetraethyl hexanoate, triethylhexanoin or the like, but not limited thereto.

In another aspect, the oil according to an exemplary embodiment of the present invention may be natural oil, synthetic oil or a mixture thereof, and more specifically, the natural oil may be any one or two or more selected from the group consisting of vegetable oils, animal oils, mineral oils and the like. As a non-limited specific example, the vegetable oil may be olive oil, almond oil, palm oil, malt oil, castor oil, avocado oil, corn oil, soybean oil, rapeseed oil, camellia oil, cottonseed oil, evening primrose oil, jojoba oil, palm oil, coconut oil, rosehip oil, macadamia oil or the like; the animal oil may be egg yolk oil, shark liver oil, emu oil, mink oil or the like; and the mineral oil may be paraffin, vaseline, ceresin or the like, but not limited thereto. The synthetic oil may be a silicone-based oil, a hydrocarbon-based oil, an ester-based oil or the like, and each of the specific components thereof is as described above for the silicone-based oil, the hydrocarbon-based oil and the ester-based oil, except for the natural oil, and thus, detailed description will be omitted.

In addition, in the present invention, in order for the core-shell capsule to have self-healing capability, it is necessary to properly adjust the content of the oil in the core. When the amount of the oil is unduly small, the solvent diffusion rate to the external phase may be too high, and when the amount of the oil is unduly large, the content of the solvent is lowered so that the solubility of the water-insoluble polymer compound may be decreased. As an example, the weight ratio of the solvent:the oil in the core may be 1:0.1 to 10. Within this range, the solvent is diffused at an appropriate rate, so that the core-shell capsule may have excellent self-healing capability, and the water-insoluble polymer compound may be well dissolved in the solvent. Preferably the weight ratio of the solvent:the oil may be preferably 1:0.5 to 5, more preferably the weight ratio of the solvent:the oil may be 1:0.8 to 2. Within this range, the water-insoluble polymer compound may be easily dissolved, and the diffusion rate of the solvent is properly adjusted, so that the solvent and the polymer compound dissolved in the solvent may be diffused to the external phase when the capsule is damaged, thereby self-healing the damaged part of the capsule more effectively.

Meanwhile, in the present invention, the core-shell capsule may have an average diameter of 0.1 to 10 mm, more preferably 0.5 to 5 mm, still more preferably 0.5 to 3 mm. Within this range, the capsule may be used as a formulation more easily.

In the present invention, the shell in the core-shell capsule may have a thickness of 1 nm to 3 mm, more preferably 2 nm to 2 mm, still more preferably 2 nm to 1 mm. Within this range, the capsule may not be easily broken with small impact, and a sense of use when applied on skin may be excellent.

In addition, another embodiment of the present invention relates to a cosmetic composition including the core-shell capsules as described above, and the cosmetic composition may include water which is an external phase together with the core-shell capsules.

Specifically, the present invention according to an exemplary embodiment relates to a cosmetic composition including core-shell capsules including: a core including an oil, a solvent satisfying the following Equation 1, and a water-insoluble polymer compound dissolved in the solvent; and a water-insoluble polymer shell surrounding the core, as an internal phase, and water as an external phase.

$$0.01 \leq C_A/C_B \leq 100 \quad \text{[Equation 1]}$$

wherein $C_A/C_B$ is a distribution coefficient of the solvent, in which when the solvent is dissolved in oil and water to reach equilibrium, $C_A$ is a concentration of the solvent dissolved in the oil, and $C_B$ is a concentration of the solvent dissolved in the water.

As described above for the core-shell capsule, as the core-shell capsule has water as the external phase, when a crack occurs in the polymer shell, the water-insoluble polymer compound dissolved in the core flows out of the damaged part of the shell to water which is the external phase, and is partially precipitated by the water at this time to restore the cracked portion of the shell, thereby self-healing the capsule shape. Accordingly, the capsule may be self-healed by itself even in the case of damage by an external impact, severe temperature change, or the like, and thus, the cosmetic composition according to the present invention may have very high stability.

In an exemplary embodiment of the present invention, the cosmetic composition may further include surfactants, sunscreen agents, antioxidants, stabilizers, pH adjusting agents, preservatives, disinfectants, coloring agents, perfumes, pearling agents, or the like which are commonly used in the art, depending on the purpose of the cosmetic composition, within the range of not deteriorating the self-healing capability of the core-shell capsule.

The cosmetic composition having such excellent self-healing capability may be used for skin, lotion, essence, cream, makeup base, foundation, concealer or the like, but not limited thereto.

Hereinafter, the core-shell capsule and the cosmetic composition according to the present invention will be described in more detail by the following Examples. However, the following Examples are only a reference for describing the present invention in detail, and the present invention is not limited thereto, and may be implemented in various forms. In addition, unless otherwise defined, all technical terms and scientific terms have the same meanings as those commonly understood by a person skilled in the art to which the present invention pertain. The terms used herein is only for effectively describing a certain exemplary embodiment, and not intended to limit the present invention. In addition, the singular form used in the specification and claims appended thereto may be intended to also include a plural form, unless otherwise indicated in the context. Further, unless otherwise stated, the unit of added materials herein may be wt %.

Example 1

Core-Shell Capsules were Prepared Using Fluidics.

Specifically, a mixed solution of 10 wt % of ethyl cellulose, 44.9 wt % of ethanol, 45 wt % of octyl dodecanol and 0.1 wt % of lithospermum erythrorhizon root extract, as an internal phase material was dispersed in water (containing 0.1 wt % of acrylate/C10-30 alkyl acrylate crosspolymer and 0.07 wt % of tromethamine) as an external phase, using fluidics, thereby preparing core-shell capsules having an average diameter of 1 mm. Here, the distribution coefficient of ethanol, $C_A/C_B$ was 0.41, and it was calculated by adding 30 g of water and octyldodecanol to two measuring cylinders, respectively, further adding 20 g of ethanol, respectively, mixing them, and measuring the volume increase ratio in the two measuring cylinders. The lithospermum erythrorhizon root extract as a coloring agent was added for easily observing release of the internal phase material and shape maintenance of the capsules.

Comparative Example 1

20 wt % of ethyl cellulose and 80 wt % of ethanol were mixed to prepare a mixed solution, from which a capsule precursor was prepared using the same manner as in Example 1, and the solvent was volatilized at high temperature to prepare empty hard capsules (only having a shell), and thereafter, the inside thereof was filled with a mixed solution of 99.9 wt % of ethanol and 0.1 wt % of corydalis incisa extract again, thereby preparing core-shell capsules.

Comparative Example 2

Core-shell capsules were prepared in the same manner as in Example 1, except for using dipropylene glycol instead of ethanol, and ferric ferrocyanide as the coloring agent. Here, almost all dipropylene glycol migrated to a water phase, so that the distribution coefficient of dipropylene glycol converged to almost 0.

Comparative Example 3

All processes proceeded in the same manner as in Example 1, except for using squalane instead of ethanol, and ferric ferrocyanide as the coloring agent, but core-shell capsules were not formed. Here, squalane hardly migrated to the water phase and remained in the oil phase, so that the distribution coefficient of squalane converged to almost infinity.

Physical Property Evaluation

1) Repeated Impact Experiment

The core-shell capsules prepared from Example 1 and Comparative Example 1 were repeatedly impacted with a needle so that the capsules were damaged.

Figure 2:
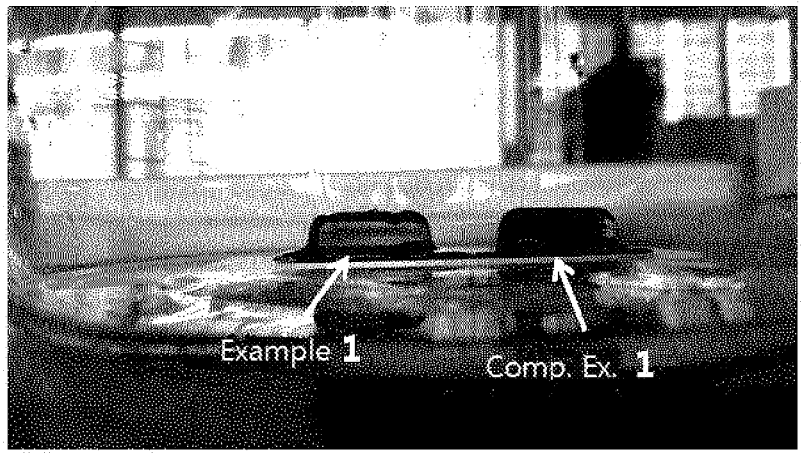
FIG. 2 is a photograph of core-shell capsules prepared according to Example 1 and Comparative Example 1, in which self-healing of the capsules when an external impact was applied is compared.
Figure 2:
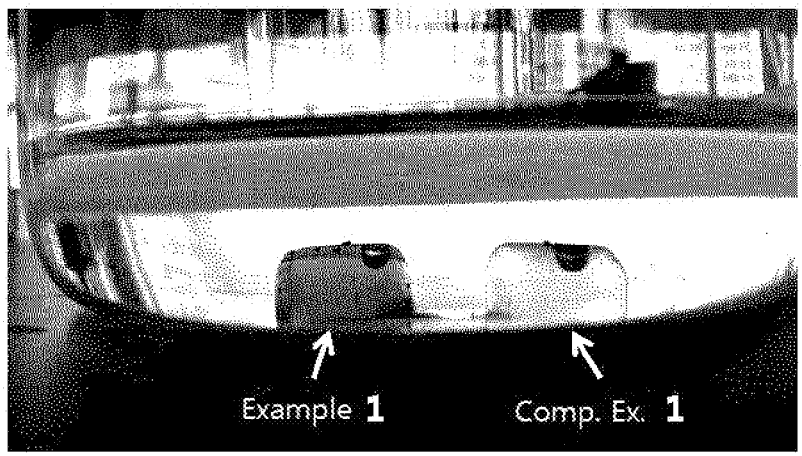

As a result, as illustrated in FIG. 2, it was confirmed in Example 1 that ethyl cellulose dissolved in ethanol was diffused in the portion of the shell cracked by repeated impact to the outside and precipitated, thereby recovering the cracked portion of the shell to maintain the capsule shape, and stably preserving the internal material.

However, it was confirmed in Comparative Example 1 that the shell was damaged by repeated impact, but since only ethanol was present as the internal material, the self-healing of the shell was impossible, and the internal material was all diffused to the outside.

2) Repeated Freezing Experiment

The core-shell capsules prepared in Example 1 and Comparative Example 2 were frozen at −20° C., and then thawed at room temperature of about 25° C., which is repeated three times.

Figure 3:
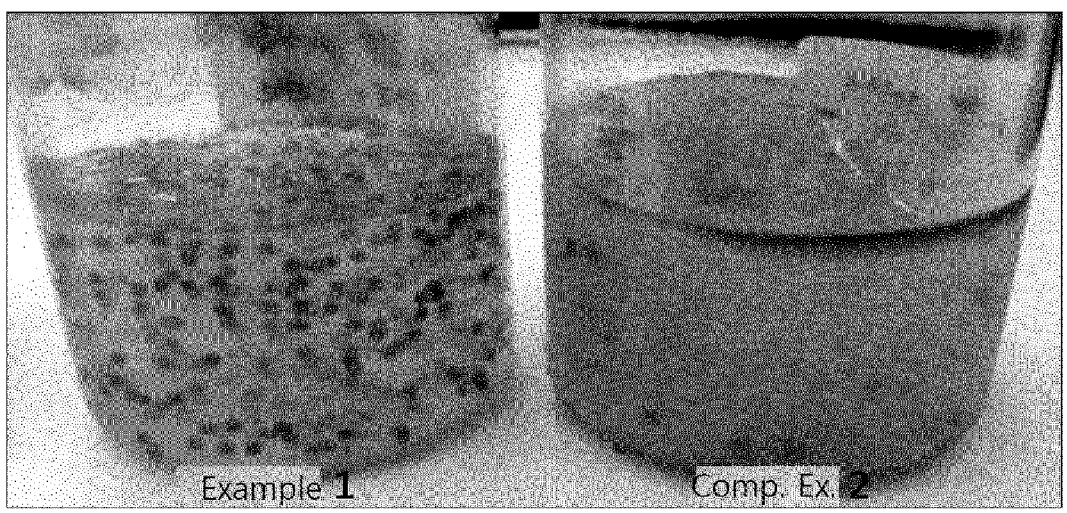
FIG. 3 is a photograph of core-shell capsules prepared according to Example 1 and Comparative Example 2, in which self-healing of the capsules when severe temperature change was applied is compared.

As a result, as illustrated in FIG. 3, it was confirmed in Example 1 that the internal phase material in the core-shell capsule was stably preserved, which shows that even in the case that the core-shell capsules were damaged by severe temperature change, the capsules were self-healed by themselves, so that the capsule shape was maintained very stably.

However, it was confirmed in Comparative Example 2 that since the capsule shape was destroyed by severe temperature change, the internal material flowed out to the outside.

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A self-healing core-shell capsule comprising:
a core including an oil, a solvent satisfying the following Equation 1, and a water-insoluble polymer compound dissolved in the solvent; and a shell surrounding the core:

$$0.01 \leq C_A/C_B \leq 100 \quad \text{[Equation 1]}$$

wherein $C_A/C_B$ is a distribution coefficient of the solvent, in which when the solvent is dissolved in oil and water to reach equilibrium, $C_A$ is a concentration of the solvent dissolved in the oil, and $C_B$ is a concentration of the solvent dissolved in the water;
wherein the oil is at least one of a silicone-based oil, a hydrocarbon-based oil, or an ester-based oil;
wherein the solvent is at least one of an alcohol-based solvent or a ketone-based solvent, and the alcohol-based solvent is at least one selected from methanol, ethanol, isopropyl alcohol, and n-propyl alcohol;
wherein the water-insoluble polymer compound is at least one of a cellulose-based polymer, a polystyrene-based polymer, or an acrylate-based polymer;
wherein a weight ratio of the water-insoluble polymer compound to the solvent in the core is 1:0.5 to 10; and
wherein the core-shell capsule has an average diameter of 0.1 to 10 mm and the water-insoluble polymer shell has a thickness of 1 nm to 3 mm.

2. A cosmetic composition comprising a self-healing core-shell capsule of claim 1.

3. The self-healing core-shell capsule of claim 1, wherein the oil is at least one silicone-based oil selected from cyclopentasiloxane, cyclohexasiloxane, cycloheptasiloxane, cyclomethicone, cyclophenylmethicone, cyclotetrasiloxane, cyclotrisiloxane, dimethicone, caprildimethicone, caprilyltrimethicone, caprilylmethicone, cetearylmethicone, hex adec ylmethicone, hexylmethicone, laurylmethicone, miristylmethicone, phenylmethicone, stearylmethicone, stearyldimethicone, trifluoropropylmethicone, cetyldimethicone, dimethylpolysiloxane, methylphenylpolysiloxane, decamethylcyclopentasiloxane, methyltrimethicone, and phenyltrimethicone.

4. The self-healing core-shell capsule of claim 1, wherein the oil is at least one hydrocarbon-based oil selected from n-octane, n-nonane, n-decane, n-undecane, n-dodecane, n-tridecane, n-tetradecane, n-pentadecane, n-hexadecane, n-heptadecane, n-octadecane, vaseline, paraffin, isoparaffin, ceresin, squalane, squalene, polybutene, polydecene, or polyisoprene.

5. The self-healing core-shell capsule of claim 1, wherein the oil is at least one ester-based oil selected from ascorbyl palmitate, ascorbyl linoleate, ascorbyl stearate, distearyl maleate, benzyl benzoate, benzyl laurate, butylene glycol dicaprylate/dicaprate, butylene glycol diisononanoate, butylene glycol laurate, butylene glycol stearate, butyl isostearate, cetearyl isononanoate, cetearyl nonanoate, cetyl caprylate, cetylethyl hexanoate, cetyl isononanoate, ethylhexyl caprylate/caprate, ethylhexyl isononanoate, ethylhexyl isostearate, ethylhexyl laurate, hexyl laurate, octyldodecyl isostearate, isopropyl isostearate, isostearyl isononanoate, isostearyl isostearate, isocetylethyl hexanoate, neopentyl glycol dicaprate, neopentyl glycol diethyl hexanoate, neopentyl glycol diisononanoate, neopentyl glycol diisostearate, pentaerythrityl stearate, pentaerythrityl tetraethyl hexanoate, and triethylhexanoin.

6. The self-healing core-shell capsule of claim 1, wherein the water-insoluble polymer compound is at least one of polystyrene, poly p-methylstyrene, poly m-methylstyrene, poly p-ethylstyrene, poly m-ethylstyrene, poly p-chlorostyrene, poly m-chlorostyrene, poly p-chloromethylstyrene, poly m-chloromethylstyrene, poly p-butoxystyrene, poly m-butoxystyrene, poly t-butoxystyrene; and wherein the acrylate-based polymer compound may be any one or two or more selected from the group consisting of polymethyl (meth)acrylate, polyethyl(meth)acrylate, polypropyl(meth)acrylate, poly n-butyl(meth)acrylate, polyisobutyl(meth)acrylate, poly t-butyl(meth)acrylate, poly 2-ethylhexyl (meth)acrylate, poly n-octyl(meth)acrylate, polylauryl (meth)acrylate, polystearyl(meth)acrylate, poly 2-hydroxyethyl(meth)acrylate, polyethyleneglycol(meth) acrylate, methoxypolyethyleneglycol(meth)acrylate, polyglycidyl(meth)acrylate, polydimethylaminoethyl(meth) acrylate, or polydiethylaminoethyl(meth)acrylate.

7. The self-healing core-shell capsule of claim 1, wherein the solvent is at least one ketone-based solvent selected from acetone, methylethyl ketone, and methylisobutyl ketone.

8. The cosmetic composition of claim 2, wherein the oil is at least one silicone-based oil selected from cyclopentasiloxane, cyclohexasiloxane, cycloheptasiloxane, cyclomethicone, cyclophenylmethicone, cyclotetrasiloxane, cyclotrisiloxane, dimethicone, caprildimethicone, capriltrimethicone, caprilylmethicone, cetearylmethicone, hex adec ylmethicone, hexylmethicone, laurylmethicone, miristylmethicone, phenylmethicone, stearylmethicone, stearyldimethicone, trifluoropropylmethicone, cetyldimethicone, dimethylpolysiloxane, methylphenylpolysiloxane, decamethylcyclopentasiloxane, methyltrimethicone, and phenyltrimethicone.

9. The cosmetic composition of claim 2, wherein the oil is at least one hydrocarbon-based oil selected from n-octane, n-nonane, n-decane, n-undecane, n-dodecane, n-tridecane, n-tetradecane, n-pentadecane, n-hexadecane, n-heptadecane, n-octadecane, vaseline, paraffin, isoparaffin, ceresin, squalane, squalene, polybutene, polydecene, or polyisoprene.

10. The cosmetic composition of claim 2, wherein the oil is at least one ester-based oil selected from ascorbyl palmitate, ascorbyl linoleate, ascorbyl stearate, distearyl maleate, benzyl benzoate, benzyl laurate, butylene glycol dicaprylate/dicaprate, butylene glycol diisononanoate, butylene glycol laurate, butylene glycol stearate, butyl isostearate, cetearyl isononanoate, cetearyl nonanoate, cetyl caprylate, cetylethyl hexanoate, cetyl isononanoate, ethylhexyl caprylate/caprate, ethylhexyl isononanoate, ethylhexyl isostearate, ethylhexyl laurate, hexyl laurate, octyldodecyl isostearate, isopropyl isostearate, isostearyl isononanoate, isostearyl isostearate, isocetylethyl hexanoate, neopentyl glycol dicaprate, neopentyl glycol diethyl hexanoate, neopentyl glycol diisononanoate, neopentyl glycol diisostearate, pentaerythrityl stearate, pentaerythrityl tetraethyl hexanoate, and triethylhexanoin.

11. The cosmetic composition of claim 2, wherein the water-insoluble polymer compound is at least one of polystyrene, poly p-methylstyrene, poly m-methylstyrene, poly p-ethylstyrene, poly m-ethylstyrene, poly p-chlorostyrene, poly m-chlorostyrene, poly p-chloromethylstyrene, poly m-chloromethylstyrene, poly p-butoxystyrene, poly m-butoxystyrene, poly t-butoxystyrene; and wherein the acrylate-based polymer compound may be any one or two or more selected from the group consisting of polymethyl(meth)acrylate, polyethyl(meth)acrylate, polypropyl(meth)acrylate, poly n-butyl(meth)acrylate, polyisobutyl(meth)acrylate, poly t-butyl(meth)acrylate, poly 2-ethylhexyl(meth)acrylate, poly n-octyl(meth)acrylate, polylauryl(meth)acrylate, polystearyl(meth)acrylate, poly 2-hydroxyethyl(meth)acrylate, polyethyleneglycol(meth)acrylate, methoxypolyethyleneglycol(meth)acrylate, polyglycidyl(meth)acrylate, polydimethylaminoethyl(meth)acrylate, or polydiethylaminoethyl(meth)acrylate.

12. The cosmetic composition of claim 2, wherein the solvent is at least one ketone-based solvent selected from acetone, methylethyl ketone, and methylisobutyl ketone.

* * * * *